United States Patent [19]

Sasisekharan et al.

[11] Patent Number: 5,569,600
[45] Date of Patent: Oct. 29, 1996

[54] **PURIFICATION, COMPOSITION AND SPECIFICITY OF HEPARINASE I, II, AND III FROM *FLAVOBACTERIUM HEPARINUM***

[75] Inventors: Ramnath Sasisekharan, Arlington, Mass.; Daniel L. Lohse, Bryan, Tex.; Charles L. Cooney, Brookline, Mass.; Robert J. Linhardt, Iowa City, Iowa; Robert S. Langer, Newton, Mass.

[73] Assignees: Massachusetts Institute of Technology, Iowa City, Iowa; University of Iowa Research Foundation, Cambridge, Mass.

[21] Appl. No.: 378,789

[22] Filed: Jan. 26, 1995

Related U.S. Application Data

[62] Division of Ser. No. 983,367, Nov. 30, 1992, Pat. No. 5,389,539.
[51] Int. Cl.$^6$ .............................. C12N 9/00; C12N 9/52; C12N 1/20
[52] U.S. Cl. .................. 435/220; 435/100; 435/183; 435/232; 435/822; 435/850
[58] Field of Search ................................ 435/100, 183, 435/220, 232, 822, 850

[56] References Cited

U.S. PATENT DOCUMENTS

| | | | |
|---|---|---|---|
| 4,341,869 | 7/1982 | Langer et al. | 435/232 |
| 4,373,023 | 2/1983 | Langer et al. | 435/2 |
| 4,396,762 | 8/1983 | Langer et al. | 536/21 |
| 4,443,545 | 4/1984 | Langer et al. | 435/232 |
| 5,169,772 | 12/1992 | Zimmerman et al. | 435/232 |
| 5,198,355 | 3/1993 | Kikuchi et al. | 435/232 |

OTHER PUBLICATIONS

Hovingh. P. and Linker, A., "The Enzymatic Degradation of Heparin and Heparitin Sulfate," *J. Biol. Chem.* 245, 6170–6175 (1970).

Yang, V. C., et al., "Purification and Characterization of Heparinase from Flavobacterium Heparinum," *J. Biol Chem.* 260, 1849–1857 (Feb. 1985).

Nakmura, T., et al., "Purification and Properties of Bacteroides Heparinolyticus Heparinase (Heparin Lyase) EC 4.2.2.7)," *J. Clin. Microbiol.* 26, 1070–1071 (1988).

Ototani, N., et al., "Purification of Heparinase and Heparitinase by Affinity Chromatography on Glycosaminoglycan-Bound AH-Sepharose 4B," *Carbohydr. Res.* 88, 291–303 (1981).

Galliher, P. M., et al., "Heparinase Production by Flavobacterium Heparinum," *Appl. Environ. Microbiol.* 41, 360–365 (1981).

Deutscher, M. P. (ed.) "Guide to Protein Purification," Methods in Enzymology 182, 603–613, 738–751.

Berger, S., et al., "Guide to Molecular Cloning Techniques," Methods in Enzymology 152, 393–399, 415–423, 432–447 (1987).

Cerbelaud, E. C., et al., "Sulfur Regulation of Heparinase and Sulfatases in *Flavobacterium heparinum*," *Appl. Environ. Microbiol.* 51, 640–646 (Mar. 1986).

Belyavsky, A., et al., "PCR-base cDNA library construction: general cDNA libraries at the level of a few cells," 17, 2919–2932 (Apr. 1989).

Yoshizawa et al., A 79,107,584 (Japan) 23 Aug. 1970 CA91:209379d.

Berstein, H., "A System for Heparin Removal," Ph.D. Massachusetts Institute of Technolgoy (1985).

Charm, S. E., et al., "Scale–up of Protein Isolation," W. B. Jakobv. ed., *Methods in Enzymology* 22, 476–490 (Academic Press, New York 1971).

Langer, R., et al., "An Enzymatic System for Removing Heparin in Extracorporeal Therapy," *Science* 217, 261–263 (Jul. 1982).

Linhardt, R. J., et al., "Immuno-Affinity Purification of Heparinase," *Int. J. Biochem.* 17(11), 1179–1183 (1985).

Linker, A., et al., "Heparinase and Heparitinase from Flavorbacteria," V. Ginsburg, ed., *Methods in Enzymology* 28, 902–911 (Academic Press, New York 1972).

Silva, M. E., et al., "Isolation and Partial Characterization of Three Induced Enzymes from Flavobacterium Heparinum Involved in the Degradation of Heparin and Heparitin Sulfates," *Biochemical and Biophysical Research Communications* 56(4) 965–972 (1974).

Yang, V., et al., "Removal of the Anticoagulant Activities of the Low Molecular Weight Heparin Fractions and Fragments with Flavobacterial Heparinase," *Thrombosis Research* 44(5), 599–610.

Stecher, et al., Ed., *The Merck Index*, Eighth Ed., 879 (1968).

*Primary Examiner*—John W. Rollins
*Assistant Examiner*—Deborah K. Ware
*Attorney, Agent, or Firm*—Arnall Golden & Gregory

[57] ABSTRACT

A single, reproducible scheme to simultaneously purify all three of the heparin lyases from *F. heparinum* to apparent homogeneity is disclosed herein. The kinetic properties of the heparin lyases have been determined as well as the conditions to optimize their activity and stability. Monoclonal antibodies to the three heparinases are also described and are useful for detection, isolation and characterization of the heparinases.

2 Claims, 5 Drawing Sheets

PURIFICATION, COMPOSITION AND SPECIFICITY OF HEPARINASE I, II, AND III FROM *FLAVOBACTERIUM HEPARINUM*

This is a divisional of copending application Ser. No. 07/983,367, issue as a U.S. Pat. No. 5,389,539, filed in the U.S. Patent & Trademark Office on Nov. 30, 1992.

BACKGROUND OF THE INVENTION

This invention generally relates to the purification and characterization of heparinase I, II, and III from *Flavobacterium heparinum* and antibodies thereto.

Heparin and heparan sulfate represent a class of glycosaminoglycans characterized by a linear polysaccharide of D-glucosamine (1→4) linked to hexuronic acid (Linhardt, R. J. (1991) *Chem. Ind.* 2, 45–50; Casu, B. (1985) *Adv. Carbohydr. Chem. Biochem.* 43, 51–134). Heparin and heparan sulfate are complex carbohydrates that play an important functional role in the extracellular matrix of mammals. These polysaccharides modulate and regulate tissue level events that take place either during development under normal situations or wound healing and tumor metastasis under pathological conditions.

Much of the current understanding of heparin and heparan sulfate sequence has relied on studies of their biosynthesis (Linhardt, R. J., Wang, H. M., Loganathan, D., and Bae, J. H. (1992) *Biol. Chem.* 267, 2380–2387; Lindahl, U., Feingold, D., and Roden, L. (1986) *Trends Biochem. Sci.* 11, 221–225; Jacobson, I., and Lindahl U. (1980) *J. Biol. Chem.* 255, 5094–5100; Lindahl, U., and Kjellen, L. (1987) in *The Biology of Extracellular Matrix Proteoglycans* (Wight, T. N., and Mecham R., eds) pp. 59–104, Academic Press, New York). Recent efforts (Linhardt, R. J., Rice, K. G., Kim, Y. S., Lohse, D. L., Wang, H. M., and Loganathan, D. (1988) *Biochem. J.* 254, 781–787; Linhardt, R. J., Turnbull, J. E., Wang, H. M., Loganathan, D., and Gallagher, J. T. (1990) *Biochemistry* 29, 2611–2617) have focused on the application of enzymatic methods to depolymerize these complex polysaccharides into oligosaccharides that could then be structurally characterized (Linhardt, et al. (1992) *Biol. Chem.* 267, 2380–2387; Linhardt, et al., (1988) *Biochem. J.* 254, 781–787; Loganathan, D., Wang, H. M., Mallis, L. M., and Linhardt, R. J. (1990) *Biochemistry* 29, 4362–4368).

Enzymatic methods for heparin and heparan sulfate depolymerization are very specific and require mild conditions giving oligosaccharide products that closely resemble the glycosaminoglycans from which they were derived. Two types of enzymes that degrade heparin and heparan sulfate glycosaminoglycans are the polysaccharide lyases from prokaryotic sources that act through an eliminative mechanism (Linhardt, R. J., Galliher, P. M., and Cooney, C. L. (1986) *Appl. Biochem Biotech.* 12, 135–176), and the glucuronidases (hydrolases) from eukaryotic sources that act through a hydrolytic mechanism.

Prokaryote degradation of heparin and heparan sulfate has primarily been studied using enzymes derived from *Flavobacterium heparinum* (Linker, A., and Hovingh, P. (1965) *J. Biol. Chem.* 240, 3724–3728; Linker, A., and Hovingh, P. (1970) *J. Biol Chem.* 245, 6170–6175); Dietrich, C. P., Silva, M. E., and Michelacci, Y. M. (1973) *J. Biol. Chem.* 248, 6408–6415; Silva, M. E., Dietrich, C. P., and Nader, H. B. (1976) *Biochem. Biophys. Acta* 437, 129–141). This bacterial degradation begins with the action of three (or possibly more) eliminases. These heparin lyases produce oligosaccharides with $\Delta_{4,5}$-unsaturated uronic acid residues a their non-reducing termini. These eliminases probably act in concert to convert heparin and heparan sulfate to disaccharides.

Heparin lyases are a general class of enzymes that are capable of specifically cleaving the major glycosidic linkages in heparin and heparan sulfate. Three heparin lyases have been identified in *Flavobacterium heparinum*, a heparin-utilizing organism that also produces exoglycuronidases, sulfoesterases, and sulfamidases that further act on the lyase-generated oligosaccharide products (Yang, V. C., Linhardt, R. J., Berstein, H., Cooney, C. L., and Langer, R. (1985) *J. Biol. Chem.* 260, 1849–1857; Galliher, P. M., Linhardt, R. J., Conway, L. J., Langer, R., and Cooney, C. L. (1982) *Eur. J. Appl. Microbiol. Biotechnol.* 15, 252–257). These lyases are designated as heparin lyase I (heparinase, EC 4.2.2.7), heparin lyase II (heparinase II, no EC number) and heparin lyase III (heparitinase EC 4.2.2.8). Although the specificities of these enzymes are not completely known, studies using partially purified enzymes with heparin, heparan sulfate, and structurally characterized heparin oligosaccharides have led to an understanding of the linkages susceptible to enzymatic cleavage (Lindhardt, et al., (1990), Lohse (1992), Rice, K. G., and Linhardt, R. J. (1989) *Carbohydr. Res.* 190, 219–233). The three purified heparin lyases differ in their capacity to cleave heparin and heparan sulfate: Heparin lyase I primarily cleaves heparin, heparin lyase III specifically cleaves heparan sulfate and heparin lyase II acts equally on both heparin and heparan sulfate (Linhardt, et al., 1986; Linhardt, et al., 1990).

Several Bacteroides sp. (Saylers, A. A., Vercellotti, J. R., West, S.E.H., and Wilkins, T. D. (1977) *Appl. Environ. Microbiol.* 33, 319–322; Nakamura, T., Shibata, Y., and Fujimura, S. (1988) *J. Clin. Microbiol.* 26, 1070–1071) also produce heparinases, however, these enzymes are not well characterized. A heparinase has also been purified to apparent homogeneity from an unidentified soil bacterium (Bohmer, L. H., Pitout, M. J., Steyn, P. L., and Visser, L. (1990) *J. Biol. Chem.* 265, 13609–13617). This enzyme differs from those isolated from *Flavobacterium heparinum* in its molecular weight (94,000), pI (9.2), amino acid composition and kinetic properties ($K_m$ of 3.4 μM and $V_{max}$ of 36.8 μmol/min, pH optimum of 7.6).

Three other heparin lyases, partially purified from Flavobacterium sp. Hp206, have molecular weights of 64,000, 100,000, and 72,000, as reported by Yoshida, K., Miyazono, H., Tawada, A., Kikuchi, H., Morikawa, K., and Tokuyasu, K. (1989) *10th Annual Symposium of Glycoconjugates*, Jerusalem, different from heparin lyases I-III.

The heparin lyases of *F. heparinum* are the most widely used and best studied (Lindhardt, (1986)). Linker and Hovingh (1970) first separated these lyase activities, fractionating a crude lyase fraction into a heparinase (heparin lyase I) and a heparitinase (heparin lyase III). Both activities were purified by 50-100-fold, but no physical characterization of these enzymes was performed.

Dietrich and co-workers (Dietrich, et al., 1973); Silva, et al., (1976); Silva, M. E., and Dietrich, C. P. (1974) *Biochem. Biophys. Res. Commun.* 56, 965–972; Michelacci, Y. M., and Dietrich, C. P. (1974) *Biochem. Biophys. Res. Commun.* 56, 973–980) and Ototani and Yosizawa (Ototani, N., and Yosizawa, Z. (1978) *J. Biochem.* (tokyo) 84, 1005–1008; Ototani, N., and Yosizawa, Z. (1979) *Carbohydr. Res.* 70, 295–306; Ototani, N., Kikiuchi, M., and Yosizawa, Z. (1981) *Carbohydr. Res.* 88, 291–303; Ototani, N., and Yosizawa, Z. (1981) *Proceedings of the 6th International Symposium on Glycoconjugates*, pp. 411–412, September 20–25, Tokyo, Japan Scientific Press, Tokyo) isolated three lyases, a heparinase (heparin lyase I) and two heparitinases, from *F. heparinum*. The heparinase acted on heparin to produce mainly trisulfated disaccharides (Dietrich, C. P., and Nader, H. B. (1974) *Biochem. Biophys. Acta* 343, 34–44; Dietrich, C. P., Nader, H. B., Britto, L. R., and Silva, M. E. (1971) *Biochem. Biophys. Acta* 237, 430–441); Nader, H. B., Porcionatto, M. A., Tersariol, I.L.S., Pinhal, M. S., Oliveira, F. W., Moraes, C. T., and Dietrich, C. P. (1990) *J. Biol. Chem.* 265,16807–16813) purified two heparitinases (called heparitinase I and II, possibly corresponding to heparin lyases II and III, although no physical properties of these enzymes were presented) and characterized their substrate specificity toward heparin and heparan sulfate. Heparitinase I degraded both N-acetylated and N-sulfated heparan sulfate while heparitinase II degraded primarily N-sulfated heparan sulfate.

McLean and Co-workers described the specificity of a partially purified heparinase II (Moffat, C. F., McLean, M. W., Long, W. F., and Williamson, F. B. (1991) *Eur. J. Biochem.* 197, 449–459; McLean, M. W., Long, W. F., and Williamson, F. B. (1985) in *Proceedings of the 8th International Symposium on Glycoconjugates*, pp. 73–74, September, Houston, Paeger Publishers, New York; McLean, M. W., Bruce, J. S., Long, W. F., and Williamson, F. B. (1954) *Eur. J. Biochem.* 145, 607–615). Although no evidence of homogeneity or any physical properties for heparinase II were presented, the broad specificity on various polymeric substrates (Moffat, et al., (1991)) identifies the enzyme as heparin lyase II (Lindhardt, et al., (1990); McLean, et al., (1985).

Linhardt et al. (1984) *Appl. Biochem. Biotech.* 9, 41–55) reported the purification of heparinase (heparin lyase I) to a single band on SDS-PAGE. Affinity purification of heparin lyase I on heparin-Sepharose failed, apparently due to degradation of the column matrix. Sufficient quantities of pure heparin lyase I for detailed characterization studies and amino acid analysis were first prepared by Yang et al. (1985). Heparin lyase I was used to prepare polyclonal antibodies in rabbits for affinity purification of heparin lyase I, but excessively harsh conditions required to elute the enzyme resulted in substantial loss of activity (Lindhardt, (1985)). Yang, V. C., Bernstein, H., Cooney, C. L., and Langer, R. (1987) *Appl. Biochem. Biotech.* 35–50)) also described a method to prepare heparin lyase I.

Seikagaku Co. has recently orally reported the molecular weights of their commercial enzymes corresponding to heparin lyase I-III to be 43,000, 84,000, and 70,000, respectively (Yoshida, K. (1991) *International Symposium on Heparin and Related Polysaccharides*, September 1–6, Uppsala, Sweden). These reports are in close agreement to the molecular weights described herein, but no details of their purification or characterization methods have been published.

Heparin lyases have been used to establish the presence of heparin in mixtures of proteoglycans (Kanwar, Y. S., and Farguhar, M. G. (1979) Presence of heparan sulfate in the glomerular basement membrane. *Proc. Natl. Acad. Sci., USA* 76, 1303–1307), to depolymerize heparin and heparan sulfate to characterize the structure of the resulting oligosaccharides (Linhardt, R. J., Loganathan, D. Al-Hakim, A., Wang, H.-M., Walenga, J. M., Hoppensteadt, D., and Fareed, J. (1990) Oligosaccharide mapping of low molecular weight heparins: structure and activity differences. *J. Med. Chem.* 33, 1639–1645; Linhardt, R. J., Rice, K. G., Kim, Y. S., Lohse, D. L., Wang, H. M., and Loganathan, D. (1988). Mapping and quantification of the major oligosaccharide components of heparin. *Biochem. J.* 254, 781–787; Merchant, Z. M., Kim, Y. S., Rice, K. G., and Linhardt, R. J. (1985). Structure of heparin-derived tetrasaccharides. *Biochem. J.* 229, 369–377; Turnbull, J. E., and Gallagher, J. T. (1988) Oligosaccharide mapping of heparan sulphate by polyacrylamide-gradient-gel electrophoresis and electrotransfer to nylon membrane. *Biochem J.* 251, 597–608), to produce low molecular weight heparin preparations with anticoagulant and complement inhibitory activities (Linhardt, R. J., Grant, A., Cooney, C. L., and Langer, R. (1982) Differential anticoagulant activity of heparin fragments prepared using microbial heparinase. *J. Biol. Chem.* 257, 7310–7313; Linhardt, R. J., and Loganathan, D. (1990a). Heparin, heparinoids and heparin oligosaccharides: structure and biological activity. In C. G. Gebelein (Ed.), *Biomimetic Polymers* (pp. 135–173). New York: Plenum Press; Sharath, M. D., Merchant, Z. M., Kim, Y. S., Rice, K. G., Linhardt, R. J., and Weiler, J. M. (1985) Small heparin fragments regulate the amplification pathway of complement. *Immunopharmacology* 9, 73–80) and to remove heparin from the circulation (Langer, et al., 1982). Heparin depolymerising enzymes are excellent tools to understand the role of heparin-like molecules in the extracellular matrix or to be used in different tissue microenvironments to modulate and alter the extracellular matrix in a highly specific manner. However, studies utilizing heparin lyases are hampered by difficulties in purifying the enzymes from *Flavobacterium heparinum*, especially with regard to separation of the three enzymes from each other (Linhardt, et al., 1985). Specifically, the capacity of heparin lyase II to cleave both heparin and heparan sulfate makes it difficult to distinguish from heparin lyase I which cleaves heparin and heparin lyase III which cleaves heparan sulfate.

Although all three of these heparin/heparan sulfate lyases are widely used, with the exception of heparin lyase I, there is no information on the purity or physical and kinetic characteristics of heparinase II and heparinase III. The absence of pure heparin lyases, resulting in ambiguities with respect to substrate specificity. This is due to contamination of other lyases in the preparation, and a lack of understanding of the optimal catalytic conditions and substrate specificity has stood in the way of the use of these enzymes as reagents for the specific depolymerization of heparin and heparan sulfate into oligosaccharides for structure and activity studies, and for use in clinical studies.

It is therefore an object of the present invention to provide a method for purification and characterization of heparinase I, heparinase II, and heparinase III.

It is a further object of the present invention to provide purified and characterized heparinase I, heparinase II, and heparinase III.

It is a still further object of the present invention to provide the conditions for optimal use and peptide map of the purified heparinase II and heparinase III.

It is another object of the present invention to provide the amino acid compositions of the three heparinases.

It is another object of the present invention to provide antibodies for heparinase I, II, and III which can be used in the purification and characterization of heparinases.

SUMMARY OF THE INVENTION

A single, reproducible scheme to simultaneously purify all three of the heparin lyases from *F. heparinum* to apparent homogeneity and free of contaminating lyases is disclosed herein. Heparin lyase I (heparinase, EC 4.2.2.7), heparin lyase II (no EC number), and heparin lyase III (heparitinase, EC 4.2.2.8) have molecular weights (by sodium dodecyl sulfate-polyacrylamide gel electrophoresis) and isoelectric points (by isoelectric focusing) of $M_r$ 42,800, pI 9.1–9.2, $M_r$ 70,800, pI 9.9–10.1, respectively. Their amino acid analyses and peptide maps demonstrate that while these proteins are different gene products they are closely related. The kinetic properties of the heparin lyases have been determined as well as the conditions to optimize their activity and stability.

The purification and characterization of heparinase II from *Flavobacterium heparinum* is described. The Michelis-Menton constants are: Heparin lyase II (with heparin), V(max)=15.04, $K_m$=9.23 μM (0,129 mg/ml); Heparin lyase II (with heparan sulfate), V(max)=46.95, $K_m$=43.43 μM (0.869 mg/ml). The approximate pI of the lyase calculated from agarose IEF using a pH gradient from 9–11 is around 8.9. The optimum temperature for heparin lyase II (both heparin and heparan sulfate) is 35° C. The activity is greater at higher temperatures but the stability is greatly reduced. The optimum pH for activity for the lyase: (with heparin), pH=7.3 and (with heparan sulfate), pH=6.9.

The purification and characterization of heparinase III (EC 4.2.2.8) from *Flavobacterium heparinum* is described. The Michelis-Menton constants are V(max)=277.01, $K_m$=109.97 μM (0.780 mg/ml). The approximate pI of the lyase was calculated from agarose IEF using a pH gradient from 9–11 and was found to be 9.2. The optimum temperatures for the heparin lyase III activity is 35° C. The activity is higher at higher temperatures for the enzyme but the stability is greatly reduced. The optimum pHs for heparin lyase III is pH=7.6. The substrate specificity of heparinase III is for the hexosamine-glucuronic acid linkages of the heparan sulfate backbone. The enzyme is a monomeric protein, very different from heparinase I and II in size and activity. It is possible to use heparinase III to release heparin-like chains in the extracellular matrix, for both sequencing and eliciting heparin based cellular response.

Salt effects were not observed for either heparinase II or heparinase III. Four different salts were used to confirm that salt effects and not ion effects were tested.

Methods for the preparation and use of monoclonal antibodies to the three heparinases are also described. The antibodies are useful for isolation, detection and characterization of the heparinases, individually and as a group, and in studies involving substrate specificity, enzyme inhibition and active site mapping.

Figure 1:
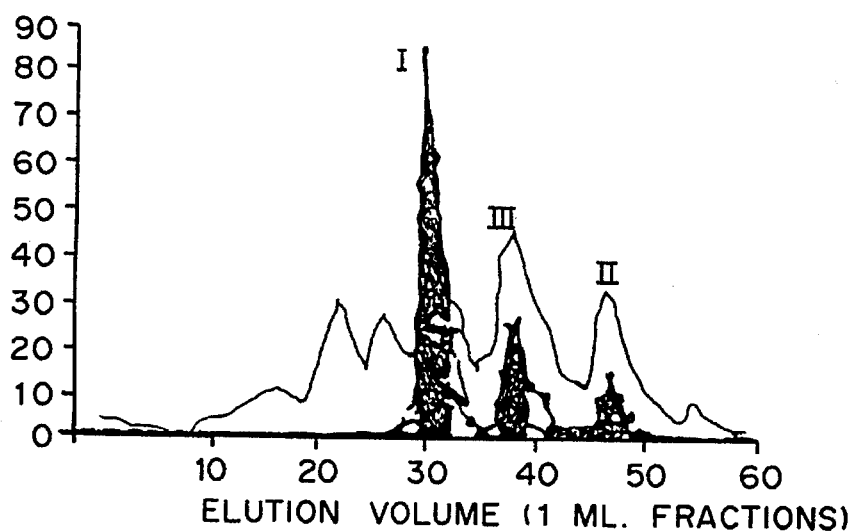
FIG. 1 is a graph of the HA-HPLC fractionation of heparin lyases. The protein ($A_{280}$) is the solid line. The activity (unit/ml) toward heparin (solid circles) and activity (unit/ml) toward heparan sulfate (solid squares) are shown with cross-hatching to indicate the portion of the peaks that were collected.

Panel B: SDS-PAGE analysis of purified heparin lyases. (a) heparin lyase I; (b) heparin lyase II; (c) heparin lyase III; (d) molecular weight markers. Arrows indicate bands of interest.

FIG. 6 is a map of the tryptic digest of heparinase II and III. Panel A is heparinase II and Panel B is heparinase III.by

DETAILED DESCRIPTION OF THE INVENTION

I. Purification and Characterization of Heparinase I, II, and III.

A single, reproducible scheme to simultaneously purify all three of the heparin lyases from *F. heparinum* to apparent homogeneity is described herein.

EXPERIMENTAL PROCEDURES

Materials

Enzyme assays and absorbance measurements were done on a UV 160 spectrophotometer from Shimadzu connected to a Fisher Scientific Isotamp model 9100 refrigerated circulating water bath. Fermentations were performed in a two-liter stirred tank fermenter from Applikon. Centrifugation was done on a Sorval RC-5 refrigerated centrifuge in a GSA rotor from Du Pont. HPLC was performed using a LDC Milton-Roy Constametric IIIG pump, a Rheodyne 7125 injector, a Jule Linear Gradient Former, and an ISCO model UA-5 absorbance monitor with a 280-nm filter. The hydroxylapatite HPLC column 1×30 cm connected in series with a 1×5 cm guard column was from Regis, the Mono-S FPLC column was from Pharmacia LKB Biotechnology Inc., the $C_{18}$ column was from Vydac, and the Bio-Sil gel permeation HPLC column was from Bio-Rad. The capillary zone electrophoresis system and the silica capillaries were from Dionex. The Mini-Protein II electrophoresis chamber, a model 1405 horizontal electrophoresis cell, and a model 1420B power source were from Bio-Rad. The tube gel electrophoresis equipment was from E-C Apparatus Corp. The precast agarose IEF gels were from Iso-labs, and the prestained molecular weight markers and the Rapid Coomassie™ stain were from Diversified Biotech. The Bio-Gel HT hydroxylapatite was from Bio-Rad and the QAE-Sephadex was from Sigma. Pressure filtration units and 25- and 43-mm PM-10 filters were from Amicon. Heparin (porcine mucosal sodium salt) was from Celsus, heparan sulfate, dermatan sulfate, and chondroitin sulfate A, C, D, and E were from Seikagaku. Bovine serum albumin, lactose, protamine (free base), bromphenol blue, naphthol red, cytochrome c (bovine heart type VA), hyaluronic acid, CAPS, bis-Tris, HEPES, TES, dithiothreitol, MOPS, mercaptoethanol, iodoacetamide, and trypsin were for Sigma. The Coomassie reagent for the protein assay was from Bio-Rad. All water used in reagents was deionized and distilled in glass.

Assays

The spectrophotometer was adjusted to the optimum temperature of the particular lyase being assayed. A 700 µl quartz microcuvette containing 400 µg of substrate in 50 mM sodium phosphate buffer (containing 100 mM sodium chloride for heparin lyase I) was thermally equilibrated. A measured quantity of lyase was added, bringing the final volume to 400 µl and the cuvette was gently mixed. The microcuvette was then immediately returned to the spectrophotometer and the change of absorbance at 232 nm was measured at 10 seconds intervals over 3 min. The activity was measured from the change of absorbance/unit time using an extinction coefficient of $3800 M^{-1}$ for products. The specific activity was then calculated by dividing the micromoles of product produced per minute by the milligrams of protein in the cuvette. The molecular weights used for heparin, heparan sulfate, and the chondroitin sulfates were 14,000, 20,000 and 25,000, respectively, Rice, K. G., and Linhardt, R. J. (1989) Carbohydr. Res. 190, 219–233. Protein concentration was measured by the Bradford assay, Bradford, M. M. (1976) Anal. Biochem. 72, 248–254, based on a bovine serum albumin standard curve.

Fermentation and Enzyme Recovery

F. heparinum (Payza, A. N., and Korn, E. D. (1956) Nature 177, 88–89) (ATCC 13125) was stored at −70° C. in a defined medium containing dimethyl sulfoxide ($Me_2SO$) (Zimmermann, J. J., Oddie, K., Langer, R., and Cooney, C. L. (1991) Appl. Biochem. Biotech. 30, 137–148). The organism was grown in a two liter stirred tank fermenter on heparin as the sole carbon source in defined medium by the method of Galliher, P. M., Cooney, C. L., Langer, R. S., and Linhardt, R. J. (1981) Appl. Environ. Microbiol. 41, 360–365). From 5 liters of fermentation broth, an 80 g wet cell pellet was obtained by centrifugation for 15 min at 12,000 x g at 4° C. This pellet was suspended in 500 ml of 10 mM sodium phosphate buffer at pH 7.0 and 4° C. Cell suspension (20 ml at a time) was placed into a 50-ml stainless steel cup and sonicated with cooling for 10 min at 100 watts using a 40% pulsed mode. The disrupted cells were centrifuged at 12,500 x g for 30 min at 4° C. and the pellet discarded. The 500 ml of supernatant, obtained by sonification and centrifugation, contained 16.3 mg/ml protein. Protamine free base (2.0 g) was dissolved in 20 ml of 10 mM sodium phosphate buffer, pH 7.0, and added dropwise with stirring to the 500 ml of supernatant. Centrifugation at 10,000 x g, at 4° C. for 20 min, removed the precipitated DNA and gave 510 ml of supernatant.

Purification of heparin Lyases from F. heparinum

Batch Hydroxylapatite Adsorption and Release

The 510 ml of supernatant containing 15.6 mg/ml protein, used directly without freezing, was divided equally into four 250 ml polypropylene centrifuge containers and placed in an ice bath. Dry hydroxylapatite (HA) (20 g) was added to each container, gently stirred, lightly compacted by centrifugation at 1000 x g for 2 min at 4° C., and the supernatant was decanted away from the HA matrix. The HA-bound protein was then resuspended in buffers having increasing concentrations of sodium phosphate and sodium chloride and recompacted by centrifugation. The supernatants were again decanted away from the matrix and assayed for enzyme activity and protein concentration. The buffers used to wash the HA matrix were prepared by mixing a solution of 10 mM sodium phosphate buffer at pH 6.8, with a solution of 250 mM sodium phosphate buffer at pH 6.8, containing 500 mM sodium chloride in ratios of 6:0, 5:1, 4:2, 3:3, 2:4, and 0:6 (v/v) at 4° C. The protein supernatant solutions were placed in dialysis tubing having a molecular weight cut-off of 14,000 and dialyzed overnight at 4° C. against 50 mM sodium phosphate buffer at pH 7.0.

QAE-Sephadex Chromatography

Lyase activity purified by batch HA was used immediately without freezing. A quaternary ammonium ethyl (QAE)-Sephadex chromatography step was performed at 4° C. Three batch HA-purified fractions (4:2; 3:3, and 2:4), having a total volume of 1.5 liters, containing more than 89% of the activity toward heparin and 88% of the activity toward heparan sulfate were consolidated (1.81 mg/ml protein and 1.72 units/ml toward heparin and 2.16 units/ml toward heparan sulfate) and applied directly in equal portions to three columns (2.5×20 cm) containing 600 ml of QAE-Sephadex. The QAE-Sephadex columns had been previously equilibrated with 50 mM sodium phosphate buffer, pH 7.0, at 4° C. Each column was then washed with 1-column volume of 50 mM phosphate buffer, pH 7.0, at 4° C. The fractions containing lyase activity that passed through the columns without interaction were collected and combined. The 2.6 liters of eluent was then concentrated to 63 ml (containing 8.23 mg/ml of protein) by Amicon pressure filtration at 60 psi and 4° C. using a 43 mm PM-10 membrane (10,000 molecular weight cut-off).

Hydroxylapatite HPLC

The 63 ml of QAE-Sephadex-purified and concentrated solution was divided into twelve 5 ml aliquots and stored at −70° C. until needed. A 5 ml sample (43 mg of protein) was removed from the freezer, allowed to thaw at room temperature, and, using a 5 ml loop, injected onto a HA HPLC column. The HA-HPLC column had been equilibrated with 50 mM sodium phosphate buffer, pH 7.0. After loading the sample, the column was washed with 50 mM sodium phosphate buffer, pH 7.0, at 0.5 ml/min, for 20 min. A 60 ml linear gradient, from 50 mM sodium phosphate, pH 7.0, to 50 mM sodium phosphate buffer containing 750 mM sodium chloride, pH 7.0, was used to elute the column. The elution was monitored continuously at 280 nm. After the gradient was complete, the column was washed with 5.0 ml of 50 mM sodium phosphate containing 1M sodium chloride, pH 7.0, to remove tightly bound proteins, and then re-equilibrated with the 50 mM sodium phosphate buffer, pH 7.0. This fractionation step was repeated with the 11 remaining aliquots. The fractions corresponding to heparin lyase I, heparin lyase II, and heparin lyase III from each of the 12 fractionations were pooled, dialyzed against 20 volumes of 50 mM sodium phosphate buffer, pH 7.0, for 12 h at 4° C., and concentrated at 60 psi and 4° C. using Amicon pressure filtration equipped with PM-10 membranes. The three lyase preparations were each divided into 1-ml aliquots and frozen at −70° C.

Mono-S FPLC of heparin Lyases I and III

The concentrated heparin lyase I and heparin lyase III preparations, isolated from HA-HPLC, were taken from the −70° C. freezer, thawed at room temperature, and applied to a Mono-S FPLC HR 5/5 cation-exchange column equilibrated with 50 mM sodium phosphate buffer, pH 7.0. A portion of each lyase preparation, 350 μl containing 1.75 mg of protein, was injected and the column washed at 1 ml/min for 5 min with 50 mM sodium phosphate buffer, pH 7.0, to elute non-interacting proteins. A linear gradient from 50 mM sodium phosphate buffer, pH 7.0, to 50 mM sodium phosphate containing 500 mM sodium chloride, pH 7.0, was used and the elution was monitored at 280 nm. The active heparin lyase I and heparin lyase III fractions were dialyzed at 4° C. against 200 mM sodium phosphate buffer, pH 7.0, for 12 h and concentrated using Amicon Pressure Filtration with a PM-10 membrane (molecular weight cut-off 10,000).

Gel Permeation HPLC

The heparin lyase I and III preparation obtained from Mono-S FPLC and the heparin lyase II preparation obtained from HA-HPLC were applied to a Bio-Sil gel permeation chromatography (GPC) HPLC column (1×25 cm) that had been equilibrated with 200 mM sodium phosphate buffer, pH 7.0. Each lyase was injected (250 μl samples containing 800 μg of protein for heparin lyases I and III; 200 μl samples containing 1.5 mg of protein for heparin lyase II), eluted at a flow rate of 1 ml/min and absorbance at 280 nm was measured. This separation was repeated 5 times for heparin lyases I-III. The active fractions were pooled together and assayed for lyase activity and protein concentration. Each heparin lyase was dialyzed against 50 mM sodium phosphate buffer, pH 7.0, concentrated at 60 psi and 4° C. using pressure filtration with 25 mm PM-10 membranes (molecular weight cut-off 10,000), and subdivided into 10 μl aliquots and stored at −70° C.

Characterization of the Three heparin Lyases

Assessment of Purity by Electrophoresis

Figure 4:
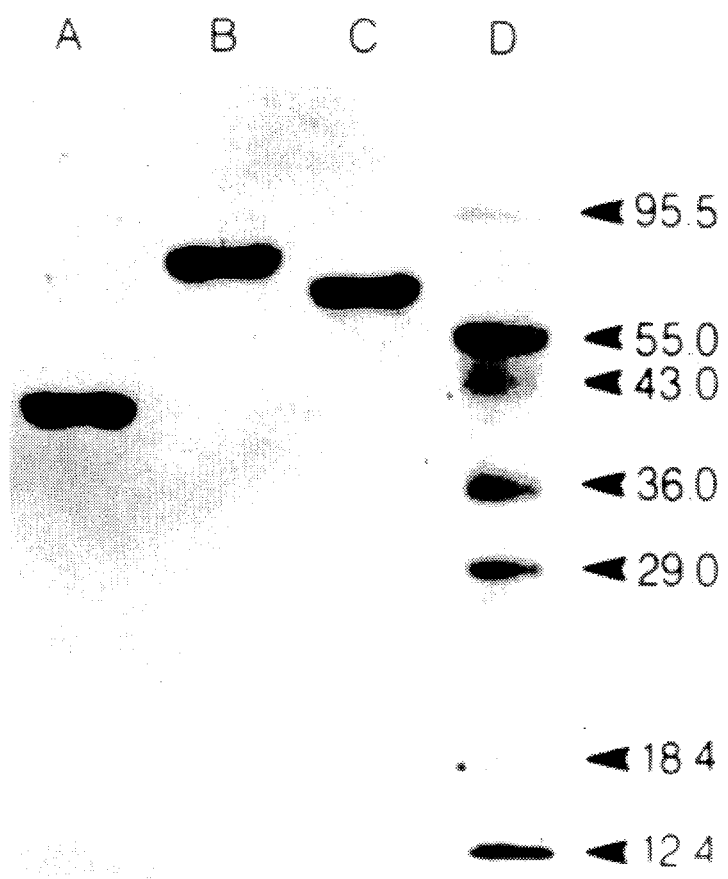
FIG. 4 is an SDS-PAGE in a 12% discontinuous polyacrylamide gel under reducing conditions. Two μg each of heparin lyase I (lane a), heparin lyase II (lane b), heparin lyase III (lane c), and molecular weight standards (lane d). Shown to the right are the mass of the molecular weight standards in kDa.

Discontinuous SDS-PAGE was performed on the three heparin lyases using a modification of a procedure previously described by Laemmli, U.K. (1970) *Nature* 227, 680–685 (FIG. 4). The gels were fixed with 12% (w/v) trichloroacetic acid, rinsed with deionized, distilled water and stained with a Rapid Coomassie Stain solution, and desrained.

IEF gel electrophoresis was run on pre-cast agarose gels (85×100 mm). Two electrode wicks were wetted with 1M phosphoric acid (anolyte) and 1M sodium hydroxide (catholyte). Electrophoresis was at 5 watts for 5 min, then at 10 watts for 1 h until the voltage was constant at 1200 V. The gel was immediately fixed in 15% aqueous trichloroacetic acid, blotted and rinsed with water, dried overnight, stained by using Coomassie G-250, and destained.

Continuous acid-urea gel electrophoresis was performed in 10% polyacrylamide tube gels (Panyim, S., and Chalkley, R. (1969) *Arch. Biochem. Biophys.* 130, 337–346). Heparin lyase I-III samples (10 μg) were prepared in acetic acid-urea buffer containing glycerol and naphthol red as a tracking dye. Electrophoresis was at a constant current of 2.5 mA/tube gel. The proteins were run toward the cathode for approximately 2 h, until the 100 μg of cytochrome c standard (a brown band) was at the bottom of its tube. Staining and destaining were accomplished as described for SDS-PAGE.

Capillary zone electrophoresis on the three heparin lyases used a Dionex Capillary Electrophoresis System on a 375 μm ×70-cm capillary by a previously published method for protein analysis (Lauer, H. H., and McManigill, D. (1986) *Anal. Chem.* 58, 166–170) in 20 mM CAPS containing 10 mM potassium chloride, pH 11.0, at 20 kV at room temperature and detection was by absorbance at 280 nm. Heparin lyase I-III samples (20 nl), each containing 2.74, 2.07, and 2.45 mg/ml, respectively, were analyzed.

Reversed-phase HPLC

Reversed-phase (RP) HPLC (HP-1090 Hewitt Packard, CA) used a Vydac $C_{18}$ column (Sasisekharan, R. (1991) Ph.D. thesis, Cloning and Biochemical Characterization of heparinase from *Flavobacterium heparinum*, Harvard University). One nmol of each purified enzyme was injected onto the RP-HPLC column and eluted using a gradient from 0 to 80% acetonitrile in 0.1 to 1 TFA, $H_2O$ for 120 min. These elution profiles were monitored at 210 and 280 nm. The enzyme peaks were isolated for amino acid analysis for composition and digestion with trypsin for peptide mapping.

Tryptic Peptide Mapping

A nanomole of each RP-HPLC-purified enzyme was denatured in 50 μl of 8M urea containing 400 mM ammonium carbonate and 5 mM dithiothreitol at 50° C. (Sasisekharan, R. (1991) Ph.D. thesis). After cooling to room temperature, the proteins were alkylated with 10 mM iodoacetamide for 15 min in the dark. The total reaction volume was 200 μl. Trypsin (4%, w/w) was added to each lyase solution, and the proteins were digested at 37° C. for 24 h. Proteolysis was terminated by heating at 65° C. for 2 min. The peptides formed in each digest were completely soluble and were injected onto RP-HPLC column and were eluted using a gradient from 0 to 80% acetonitrile in 120 min. The tryptic peptide maps were monitored at 280 nm.

Amino Acid Compositional and N-terminal Analysis

Amino acid compositional analysis was performed at the Biopolymers Laboratories at the Massachusetts Institute of Technology on an Applied Biosystems model 420/130 Derivatizer/Amino Acid Analyzer using Phenylisothiocyanate pre-column derivatization chemistry. Gas-phase hydrolysis of samples was performed using a Waters Pico Tag Hydrolysis Workstation. In pre-column derivatization, free amino acids are coupled with phenylisothiocyanate to form phenylthiocarbamyl amino acids that were detected at 254 nm as they eluted from the reversed-phase column. Hydrolysis used 6N hydrochloric acid, 0.1% phenol at either 155° C. for 1 h or 100° C. for 22 h. Hydrolysis times of 36 and 48 h were also examined to ensure that the protein was being fully hydrolyzed with minimum destruction of amino acid residues N-terminal analysis was done on 1 nmol of heparin lyase I-III.

Effect of pH on Activity

The activity pH optimum for each of the lyases was obtained by using succinic acid (4.0–6.5), bis-tris propane (BTP)-HCl (6.5–9.0) and both Tris-HCl and sodium phosphate (6.0–7.5). Heparin lyase I-III assay solutions were made by diluting a 10-μl sample of the purified lyase (2–3 mg/ml protein concentration) with 90 μl of sodium phosphate buffer at 50 mM, pH 7.0, and placed on ice until required for assay. The activities of each lyase (I acting on heparin, II acting on both heparin and heparan sulfate, and III acting on heparan sulfate) were then determined at different pH values.

Buffer Selection for Optimum Activity

The buffer giving optimum activity for each heparin lyase was selected by testing buffers with buffering capacity near the pH optima calculated in the previous experiments. These buffers were: Tris-HCl, sodium phosphate, HEPES, MOPS, TES, and BTP-CHl. Each buffer was prepared at 50 mM, and its pH was adjusted with hydrochloric acid or sodium hydroxide to 6.9 for heparin lyase II acting on heparin, 7.15 for heparin lyase I, 7.3 for heparin lyase II acting on heparan sulfate, and 7.6 for heparin lyase III. The heparin lyase assay solutions were made by diluting enzyme in 50 mM sodium phosphate buffer adjusted to the appropriate pH as previously described. Heparin lyase activity was determined in each buffer. Activity was assayed both immediately after addition to each buffer and following incubation for 24 h at 37° C.

Affect of Divalent Metals and Added Salt on Activity

BTP-HCl buffer (50 mM) was prepared containing either 10 mM calcium chloride, 10 μM or 1 mM copper (II) chloride, 10 μM and 1 mM mercury (II) chloride, and 1 mM zinc (II) chloride. Each solution was adjusted to the optimum pH for the lyase being tested, and the activity of the heparin lyases was measured in the presence and absence of divalent metals.

The salt concentration for optimum activity was investigated. Sodium chloride, potassium chloride, and sodium and potassium acetate were used to differentiate between ionic strength and specific ion affects. Added salt concentrations varied between 0 and 500 mM and were prepared in 50 mM sodium phosphate buffer after which the pH was adjusted to each enzyme's optimum and the heparin lyase activity was measured.

Temperature for Optimum Activity

Temperature for optimum activity was determined for the heparin lyases at their optimum pH in sodium phosphate buffer (the heparin lyase I assay buffer contained 100 mM sodium chloride) in 5° increments at temperatures between 15° and 55° C. The temperature was adjusted in a temperature-regulated spectrophotometer and equilibrated for 10 min before the assay was started.

Temperature Stability Optima

Lyase assay stock solutions were prepared in the appropriate buffer and placed in water baths at the following temperatures: heparin lyase I at 30° C., heparin lyase II at 35° C., and heparin lyase III at both 35° and 40° C. Small aliquots were taken out at various time intervals (1–22 h) to measure remaining enzyme activity.

Determination of Kinetic Constants

Michaelis-Menten constants were determined using the optimized conditions. The final absorbance value for total depolymerization was divided by 20 to find a value that represented 5% reaction completion. The purified lyase preparations were diluted so that 5% of total depolymerization would be reached only at the end of a 3-min assay. The reaction velocities at specific molar concentrations for each lyase and their substrates were used for kinetic analysis using EZ-FIT hyperbolic curve-fitting program of Perella, F. W. (1988) *Anal. Biochem.* 174, 437–447). Substrate solutions were prepared from 50 mg/ml heparin and 40 mg/ml for heparan sulfate stock solutions. These constants were determined at 30° C. in 50 mM sodium phosphate buffer at pH 7.15 containing 100 mM sodium chloride for heparin lyase I and 35° C. for heparin lyase II in 50 mM sodium phosphate buffer at pH 7.3 for heparin and pH 6.9 for heparan sulfate and at 35° C. in 50 mM sodium phosphate buffer at pH 7.6 for heparin lyase III.

Activity of the heparin Lyases on Complex Polysaccharides

Each heparin lyase was added to a solution of complex polysaccharides (1 mg/ml) under optimized assay conditions, and the reaction was monitored at 232 nm for 30 min. The amount of purified lyase used was sufficient for complete depolymerization of heparin or heparan sulfate substrates within 30 min. The initial rate of depolymerization of each polysaccharide was measured, the reaction was then continued for 24 h, and the final level of polysaccharide depolymerization was assessed by measuring the final absorbance at 232 nm and expressed as percent activity.

Stability of the Heparin Lyases

Heparin lyase stabilities toward freeze thawing and lyophilization were investigated using two excipients, bovine serum albumin (BSA) at 2 mg/ml and lactose at 0.5 wt %. Each lyase was either dissolved in 50 mM sodium phosphate buffer, 50 mM sodium phosphate buffer containing 2 mg/ml BSA, or 50 mM sodium phosphate buffer containing 0.5% lactose at concentrations of 1–3 units/ml. These lyase solutions were then divided into 3 equal aliquots, and one of each was subjected to either freeze thawing, lyophilization, or retained as a control in an ice bath. The activities of heparin lyases I-III were determined in the presence and absence of excipients after: 1) brief storage at 4° C.; 2) freezing at −70° C. and thawing; and 3) −70° C. freezing, lyophilization, and reconstituting with an equal volume of cold water.

RESULTS

Figure 2A:
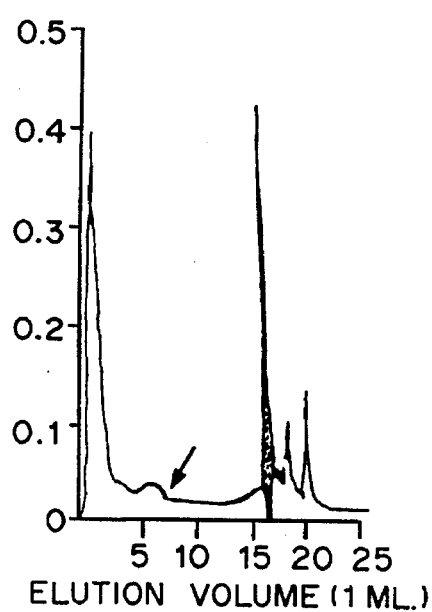
FIG. 2 is Mono-S FPLC fractionation of heparin lyases: a, heparin lyase I, and b, heparin lyase III. The arrow indicates the start of the salt gradient elution, and the cross-hatching indicates the portion of the peaks that were collected.
Figure 2B:
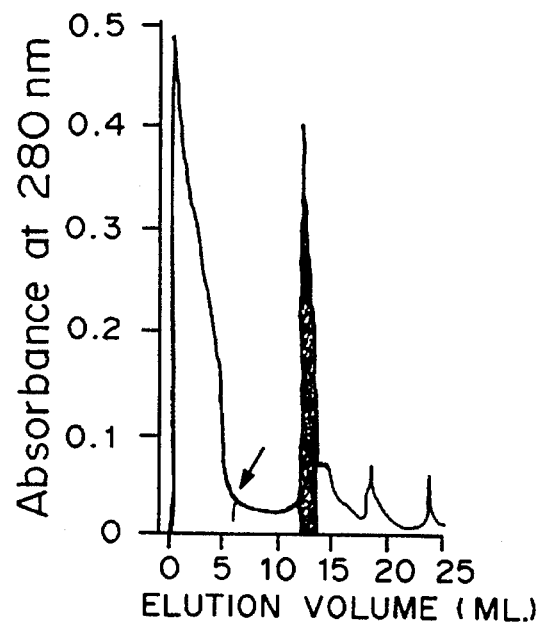
Figure 3A:
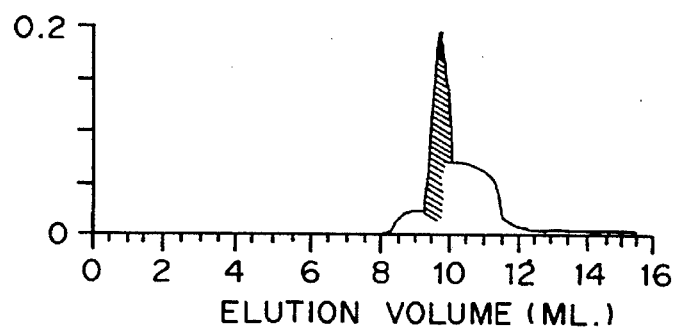
FIG. 3 is a GPC-HPLC fractionation of heparin lyases. a, heparin lyase I; b, heparin lyase II; c, heparin lyase III; and d, molecular weight standards ($M_r$) consisting of thyroglobulin (bovine, 670,000), gamma globulin (158,000), ovalbumin (44,000), myoglobin (horse, 17,000), and cyanocobalamin (1350). The cross-hatching indicates the portion of the peaks that were collected.
Figure 3B:
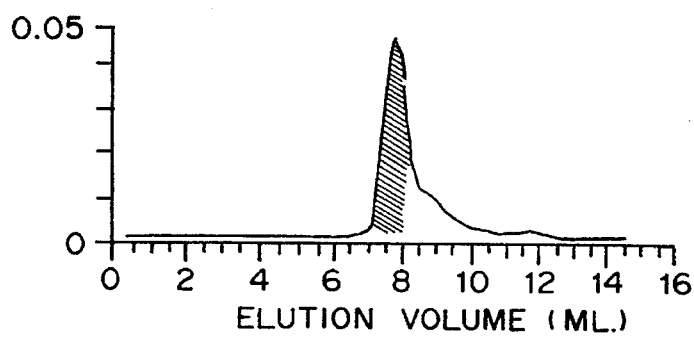
Figure 3C:
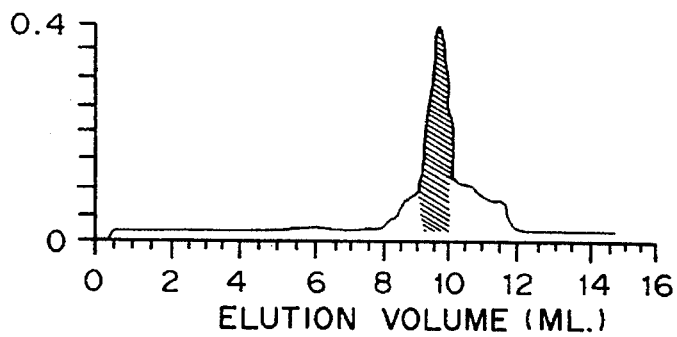
Figure 3D:
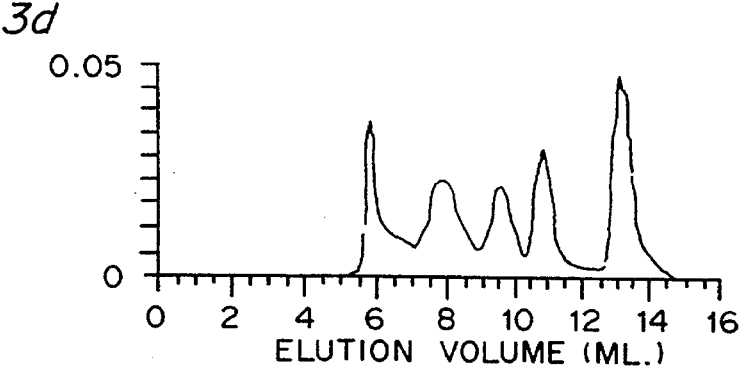

Optimized cell lysis of *F. heparinum* by sonication was accomplished in 10 min at 100 watts using a 40% pulse mode without inactivation of the liberated enzyme. Protamine precipitation increases both the total and specific activity by 42-fold without decreasing protein concentration, presumably by removing the polyanionic nucleic acids that may competitively inhibit the heparin lyases. A batch HA purification step greatly reduces the protein concentration and other contaminating activities associated with heparin/heparan sulfate metabolism, but does not separate the three heparin lyase activities. QAE-Sephadex is used to remove contaminating acidic proteins. HA-HPLC resolves the three lyase activities. A linear sodium chloride gradient is used to elute heparin lyases I-III at 330, 555, and 435 mM sodium chloride, respectively, as shown in FIG. 1. Chondroitin/dermatan sulfate lyases, also found in this bacterium, elute from the HA-HPLC column at the end of the gradient, just behind heparin lyase II. This technique gave good recovery of total heparin lyase activity while reducing protein concentration. Heparin lyases I and III were further purified by cation exchange FPLC, as shown in FIG. 2. Heparin lyase I is recovered with excellent retention of activity and a large decrease in protein concentration. The specific activity of heparin lyase III does not improve using Mono-S FPLC, as it showed a substantial reduction in total activity. SDS-PAGE analysis, however, revealed an improvement in the purity of heparin lyase III following this step. Heparin lyase II was not purified by Mono-S FPLC, since it does not bind to the column. In the final purification step, heparin lyases I-III were fractionated using GPC, as shown in FIG. 3.

Following GPC each heparin lyase preparation was shown to be homogeneous by SDS-PAGE, acid-urea PAGE, IEF, capillary zone electrophoresis, and reverse phase HPLC. The molecular weights estimated by SDS-PAGE from heparin lyases I-III were 42,800, 84,100, and 70,800, respectively.

The results obtained using this purification scheme for the three heparin lyases are summarized in Table I. Heparin lyase I was purified 3400-fold over the cell homogenate. The scheme provided on overall yield based on mass of 0.03%, a yield based on total activity recovery of 10.8%, and had a specific activity of 130 units/mg. Heparin lyase II was purified 5200-fold over the cell homogenate with an overall yield based on a mass of 0.02%. This enzyme had a specific activity of 19 units/mg toward heparin with a 1.02% total activity recovery. This enzyme preparation also had a specific activity of 36.5 units/mg toward heparan sulfate, a 1.54% total activity recovery. Heparin lyase III was purified 5100-fold over the cell homogenate, a yield of based on mass of 0.02%, a yield based on total activity of 2.74%, and had a specific activity of 63.5 units/mg.

TABLE I

Purification summary of the heparin lyases

| Purification step | Protein mg | Activity units | Unit/mg | % Activity |
|---|---|---|---|---|
| Heparin lyase I | | | | |
| Cell homogenization | 8150 | 66 | $8.12 \times 10^{-3}$ | |
| Protam Ppt. | 7960 | 2890 | $3.63 \times 10^{-1}$ | 100 |
| Batch-HA | 2720 | 2580 | $9.50 \times 10^{-1}$ | 89.4 |
| QAE Sepharose | 519 | 2220 | 4.27 | 76.8 |
| HA-HPLC | 22.6 | 944 | 41.8 | 32.7 |
| Mono-S FPLC | 7.36 | 877 | 119 | 30.4 |
| GPC-HPLC | 2.40 | 313 | 130 | 10.8 |
| Heparin lyase II acting on heparin | | | | |
| Cell homogenization | 8150 | 66 | $8.12 \times 10^{-3}$ | |
| Protam Ppt. | 7960 | 2890 | $3.63 \times 10^{-1}$ | 100 |
| Batch-HA | 2720 | 2580 | $9.50 \times 10^{-1}$ | 89.4 |
| QAE Sepharose | 519 | 2220 | 4.27 | 76.8 |
| HA-HPLC | 19.6 | 109 | 5.53 | 3.8 |
| GPC-HPLC | 1.55 | 29.4 | 19 | 1.02 |
| Heparin lyase II acting on heparan sulfate | | | | |
| Cell homogenization | 8150 | 91.5 | $1.13 \times 10^{-2}$ | |
| Protam Ppt. | 7960 | 3680 | $4.63 \times 10^{-1}$ | 100 |
| Batch-HA | 2720 | 2580 | 1.19 | 88.0 |
| QAE Sepharose | 519 | 2220 | 4.11 | 57.8 |
| HA-HPLC | 19.6 | 275 | 14 | 7.46 |
| GPC-HPLC | 1.55 | 56.5 | 36.5 | 1.54 |
| Heparin lyase III | | | | |
| Cell homogenization | 8150 | 91.5 | $1.13 \times 10^{-2}$ | |
| Protam Ppt. | 7960 | 3860 | $4.63 \times 10^{-3}$ | 100 |
| Batch-HA | 2720 | 3420 | 1.19 | 88.0 |
| QAE Sepharose | 519 | 2130 | 4.11 | 57.8 |
| HA-HPLC | 23.1 | 1010 | 43.6 | 27.4 |
| Mono-S FPLC | 8.41 | 348 | 41.4 | 9.45 |
| GPC-HPLC | 1.59 | 101 | 63.5 | 2.74 |

Characterization of heparin. Lyase Purity and Physical Properties

The physical, kinetic, and stability characteristics of the three heparin lyases were investigated. Discontinuous SDS-PAGE (Laemmli, U.K. (1970)) illustrated the three heparin lyases were apparently homogeneous. The molecular weights of heparin lyase I, III were estimated at 42,800, 84,100, and 70,800, respectively. Nonreducing SDS-PAGE without β-mercaptoethanol revealed the same banding pattern, suggesting that no subunits were present. IEF was used to determine the isoelectric points of the three heparin lyases and to assess their purity. IEF using a variety of pH gradients (pH 3–10, 7–10, and 8.5–10.5) failed to give accurate pI values for the three lyases as they each migrated to a position very near the cathode. An agarose gel with a pH gradient of 9–11 was then used, focusing the three proteins below the band for cytochrome c standard (pI=10.25). The pI values measured for heparin lyases I-III were 9.1–9.2, 8.9–9.1, and 9.9–10.1, respectively. Urea-acetic acid PAGE in tube gels, using the method of Panyim, S., and Chalkley, R. (1969), confirmed the homogeneity of the three heparin lyases. Capillary zone electrophoresis electropherograms (Lauer, H. H., and McManigill, D. (1986)) of each heparin lyase gave a single symmetrical peak. Heparin lyases I-III had migration times of 12.7, 12.4, and 13.4 min, respectively.

RP-HPLC was used to desalt the three heparin lyases prior to amino acid compositional analysis and tryptic digestion for peptide mapping (Sasisekharan, R. (1991) Ph.D. thesis). Interestingly, each chromatogram shows a very tight doublet of peaks suggesting the presence of isoforms, possibly due to post-translational modification. Amino acid analysis of heparin lyase isoforms for I, II, and III were identical. The isoforms differ slightly in hydrophilicity, possibly due to some post-translational modification such as glycosylation or phosphorylation. The major isoform of heparin lyases I-III had retention times of 38.5, 44.3, and 42.7 min, respectively, in a RP-HPLC.

Figure 6A:
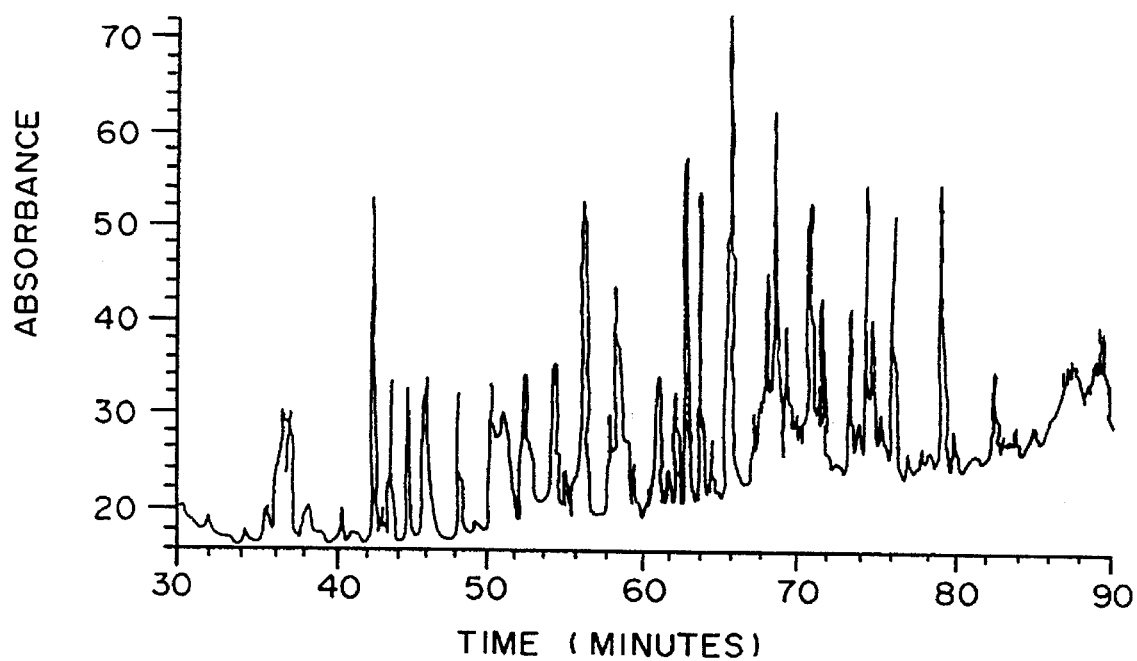
Figure 6B:
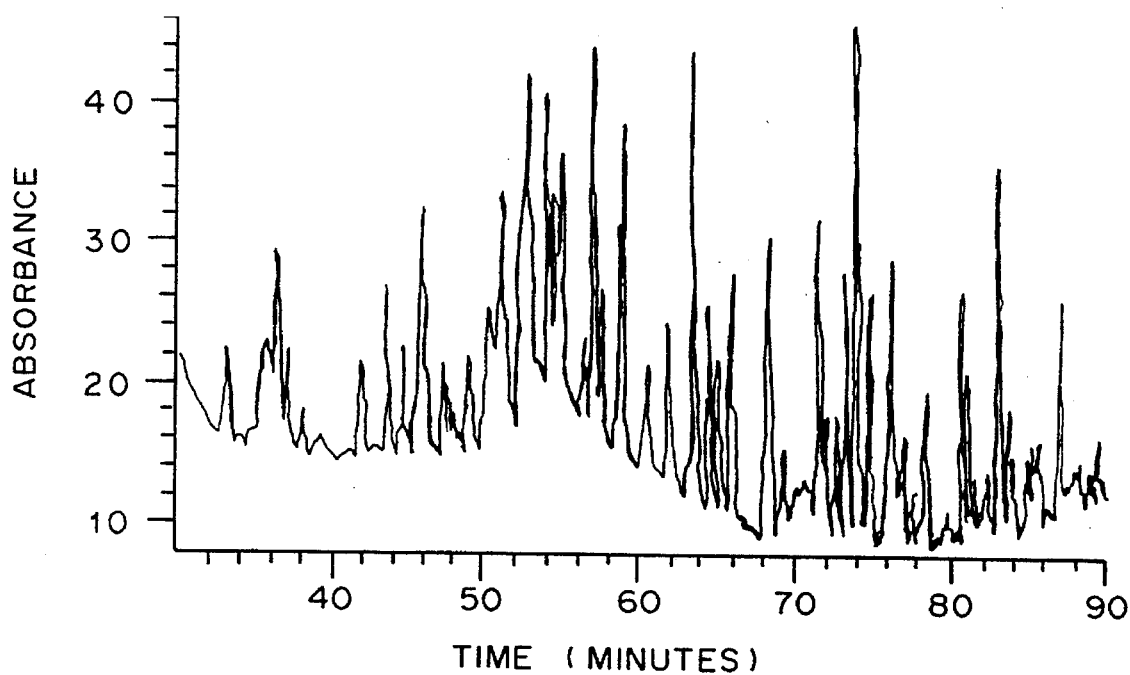

The major RP-HPLC peak corresponding to each heparin lyase was treated exhaustively with trypsin to prepare peptide fragments. These peptide fragments were again analyzed using RP-HPLC. As shown in FIG. 6A and 6B, the peptide map of each lyase was distinctly different although a few common peptide fragments were observed.

Amino acid analyses of the three heparin lyases are shown in Table II. The N-terminal amino acid is modified and hence cannot be detected by amino acid sequencing for all three lyases.

The amino acid composition and peptide mapping demonstrate that heparin lyases I-III are different gene products and that heparin lyases I and III are not merely post-translationally processed from the larger heparin lyase II.

The lyases all contain a high amount of lysine that may contribute to their high isoelectric points. Computer modeling, using the amino acid composition of heparin lyase I, gave a calculated isoelectric point of 9.33 in agreement with the experimental values obtained by using isoelectric focusing.

TABLE II

Amino Acid Composition for Heparinase I, II and III

| Amino Acid | Heparinase I | Heparinase II | Heparinase III |
|---|---|---|---|
| ASX | 45 | 91 | 95 |
| GLX | 36 | 62 | 67 |
| SER | 24 | 37 | 38 |
| GLY | 30 | 101 | 50 |
| HIS | 6 | 14 | 13 |
| ARG | 13 | 37 | 35 |
| THR | 20 | 35 | 25 |
| ALA | 26 | 55 | 52 |
| PRO | 20 | 40 | 35 |
| TYR | 27 | 54 | 37 |
| VAL | 18 | 44 | 37 |
| MET | 2 | 15 | 7 |
| ILE | 20 | 31 | 24 |
| LEU | 17 | 53 | 42 |
| PHE | 17 | 35 | 36 |
| LYS | 47 | 47 | 40 |

Assuming 727 amino acids for heparinase II (84,000 daltons), and 636 amino acids for heparinase III (70,000 daltons). Cys and Trp not reported.

Characterization of Optimal Catalytic Activity for the Heparin Lyases

The optimal reaction conditions for each of the three heparin lyases was determined in a series of experiments. The first parameter examined was the pH optimum. A heparin concentration of 2.5 mg/ml for heparin lyases I and II and a heparan sulfate concentration of 1.0 mg/ml for heparin lyases II and III were demonstrated to be saturating based on published values (14, 26) and preliminary experiments. A reaction temperature of 37° C. was initially chosen as an average of values reported in the literature (Linhardt, R. J., Turnbull, J. E., Wang, H. M., Loganathan, D., and Gallagher, J. T. (1990); Silva, M. E., Dietrich, C. P., and Nader, H. B. (1976); Yang, V. C., Linhardt, R. J., Berstein, H., Cooney, C. L., and Langer, R. (1985)). The temperature was later modified after the optimum for each lyase was determined.

The pH optima determined were 7.15 on heparin for lyase I, 7.3 on heparin and 6.9 on heparan sulfate for lyase II, and 7.6 on heparan sulfate for lyase III.

The buffer giving optimum activity for each heparin lyase was selected using six different buffers each adjusted to the optimum pH for the enzyme and substrate being studied. Heparin lyase I showed similar initial reaction velocities in Tris-HCl and BTP-HCl, intermediate activity in sodium phosphate, and reduced activity in MOPS, TES, and HEPES. After incubation in each buffer at 37° C. for 24 h, the activity was reduced to 1–20% of its initial value. Heparin lyase I incubated in MOPS, TES, and HEPES retained the most activity. Heparin lyase II activity on heparin was remarkably similar in all six buffers. When acting on heparan sulfate, however, heparin lyase II also showed a marked reduction of activity in MOPS, TES, and HEPES. After incubation in each buffer, MOPS, TES, and HEPES were found to best protect heparin lyase II activity (30–70% retention of activity) toward both heparin and heparan sulfate. Heparin lyase III showed only slight differences in activity in the six buffers studied. MOPS and HEPES protected heparin lyase III activity (15–30% retention of activity) following incubation.

The affect of calcium, copper (II), mercury (II), and zinc (II) ions on heparin lyase initial reaction velocities were investigated based on prior literature (Silva, M. E., Dietrich, C. P., and Nader, H. B. (1976); Hovingh, P., and Linker, A. (1970)). BPT-HCl buffer (50 mM) was chosen because of its compatibility with these ions.

The ionic strength (0–500 mM) for optimum activity was investigated for each heparin lyase at its pH optimum in 50 mM sodium phosphate buffer. Sodium chloride, potassium chloride, sodium acetate and potassium acetate gave comparable activities at the same ionic strength. Heparin lyase I showed increased activity in response to increased salt concentrations, with an optimum activity at 100 mM. Heparin lyases II and III each show a decrease in activity with increasing concentration of added salt. At 400 mM of salt, the activity heparin lyase I-III were almost completely inhibited.

The temperature for optimum activity was determined for the heparin lyases in 50 mM sodium phosphate buffer at their optimum pH (with heparin lyase I containing 100 mM sodium chloride) using temperatures between 15° and 55° C. The temperatures for maximum activity were 35° C. for heparin lyase I, 40° C. for heparin lyase II acting on both heparin and heparan sulfate, and 45° C. for heparin lyase III. The temperature stability optima for the heparin lyases were established to ensure that thermal inactivation did not influence experiments aimed at determining the kinetic constants. Heparin lyases I and III (protein concentration of 650 ng/ml) showed an exponential decrease in activity. Heparin lyase I lost 80% of its activity in 5 h at 30° C. Heparin lyase III lost 80% of its activity in 3.5 h and 0.5 h at 35° C. and 40° C., respectively. Heparin lyase II (protein concentration 1–2 µg/ml) showed a much slower decay in activity, retaining 70% of its activity on both heparin and heparan sulfate after 25 h at 35° C. All further studies on heparin lyase I-III used 30, 35, and 35° C., respectively, to retain high activity while maintaining enzyme stability.

The heparin lyases showed less than 0.5% activity toward chondroitin sulfate C and dermatan sulfate and no activity toward chondroitin sulfate A, D, and E. No hyaluronidase, glucuronidase activity and less than 0.5% sulfatase activity was observed.

The specificity of the three heparin lyases was examined using their polysaccharide substrates. The initial rate and the final level of heparin and heparan sulfate depolymerization was measured. Heparin lyase I-III acted at an average of 7, 14, and 1 sites in the heparin polymer and 5, 25, and 20 sites in the heparan sulfate polymer, respectively. Heparin lyase II acted on heparan sulfate at 1.7 times the initial rate observed on heparin. Oligosaccharide maps, in which the oligosaccharide products are analyzed by strong anion-exchange HPLC and gradient PAGE (Linhardt, R. J., Turnbull, J. E., Wang, H. M., Loganathan, D., and Gallagher, J. T. (1990)), were prepared for each heparin lyase acting on heparin and heparan sulfate (Lohse, D. L. (1992) Ph.D. thesis, The Heparin lyases of *Flavobacterium heparinum*, The University of Iowa). These data are consistent with the specificity for heparin lyase I-III shown in FIG. 5.

Determination of the Michaelis-Menten Constants for the Heparin Lyases

Michaelis-Menten constants were determined using the optimum reaction conditions in experiments designed to calculate reaction velocities at each substrate concentration where less than 10% had been consumed (Table III).

Stability of heparin Lyases

It was necessary to study conditions for the optimal storage of the heparin lyases as the literature is replete with examples of the instability of these enzymes. In the absence of excipient, heparin lyase I stored at 4° C., after a single freeze-thawing and after freeze-drying, retained 50, 45, and 25% of its activity, respectively. The addition of 2.0 mg/ml BSA enhanced storage stability, resulting in greater than 85% retention of activity, as did the addition of 5% lactose, giving 40–80% retention of activity. Heparin lyase II retained greater than 75% of its activity under all storage conditions, and the addition of BSA or lactose gave little additional stabilization. Heparin lyase III is very unstable toward freeze-thawing and lyophilization. Heparin lyase III retains most of its activity during brief storage at 4° C. but lost 70–80% on freeze-thawing or freeze-drying. The presence of BSA increases the recovered activity by 20–25% but added lactose destabilizes heparin lyase III.

TABLE III

Kinetic constants of the purified heparin lyases

| Heparin lyase | Substrate | $K_{m(app)}$[a] | $V_{max}$[a,b] | $K_{cat}/K_m$[c] |
|---|---|---|---|---|
| Heparin | I | 17.8 ± 1.50 | 219 ± 3.48 | 8.82 |
| Heparin | II | 57.7 ± 6.56 | 16.7 ± 0.555 | 0.405 |
| Heparan sulfate | II | 11.2 ± 2.18 | 28.6 ± 1.26 | 3.57 |
| Heparan sulfate | III | 29.4 ± 3.16 | 141 ± 3.88 | 5.59 |

[a]Values of the apparent $K_m$ and $V_{max}$ are derived from initial velocities obtained at eight or more concentrations (3–500 µM) of either heparin or heparan sulfate. Protein concentrations for heparin lyases I-III were 80, 994 and 68 ng/ml, respectively. Standard errors of apparent $K_m$ and $V_{max}$ values indicate the precision of fitting the initial rates and corresponding concentrations of heparin or heparan sulfate to the Michaelis-Menten equation as descibed under "Materials and Methods."
[b]$V_{max}$ is expressed as µmol/min mg protein.
[c]$K_{cat}/K_m$ is expressed as $(s-\mu M)^{-1}$.

The pH optimum calculated for heparin lyase I was 7.15. This value was higher than the pH of 6.5 reported by Yang et al. (1985) and by Linker and co-workers (Hovingh and Linker, (1965 and 1970)). Both groups assayed their lyase preparations using time periods of up to 6 h where thermal instability might become a factor. The maximum time period used in this study was only 3 min. The pH optimum of heparin lyase II acting on heparan sulfate was 6.9. The pH optimum for heparin lyase III was 7.6. Hovingh and Linker as well as Dietrich and co-workers reported the pH optimum of between 6.0 and 7.0 for this enzyme. Again, the assay time intervals used by both groups were up to 6 h, and the thermal instability might account for the differences between these values.

The activity of heparin lyase I is slightly reduced by 1 mM zinc and markedly reduced by 10 μM and 1 mM mercury and 1 mM copper. Calcium at 10 mM increased activity by 30%. The activity of heparin lyase II acting on both heparin and heparan sulfate in the presence of divalent metal ions showed inhibition by all of the metals tested except for 10 μM copper. Even calcium resulted in dramatically reduced heparin lyase II activity. Heparin lyase III was activated (20%) by calcium, unaffected by copper and mercury (both at 10 μM), and inhibited by zinc, mercury, and copper (all at 1 mM). In general, the addition of divalent metal ions decreased the activity of the heparin lyases. Optimal activity of heparin lyase I was observed at an ionic strength of 100 mM. Heparin lyases II and III activity decreases with increasing salt concentrations.

Table III summarizes the apparent Michaelis-Menten constants for heparin lyases I-III acting on heparin and heparan sulfate. Apparent $K_m$ values for heparin lyase I ranging from 0.3 to 42 μM and a $V_{max}$ of 19.7 μmol/min/mg protein have been reported (Rice, et al., (1989); Yang, et al., (1985); Lindhardt, (1984)). An apparent $K_m$ of 5.7 μM and $V_{max}$ of $3.57 \times 10^{-3}$ μmol/min for a purified heparin lyase III acting on heparin sulfate have been reported (Rice and Lindhardt, (1989)).

Heparin lyase I and II act on both heparin and heparan sulfate while heparin lyase III acts only on heparan sulfate. All three enzymes act endolytically, however, all cleavable sites within the polymer may not be equally susceptible (Cohen, D. M. and Linhardt, R. J. (1990) Biopolymers 30, 733–741). The primary linkages within these polymeric substrates that are cleaved by each enzyme were deduced from oligosaccharide mapping experiments. The specificity of pure heparin lyase I-III toward heparin and heparan sulfate were identical to that previously reported for their partially purified, commercially prepared counterparts. Oligosaccharide substrates (i.e., tetrasaccharides and hexasaccharides) having equivalent sites are poor substrates. The $V_{max}/K_m$ observed for heparin lyase I and III acting on tetrasaccharide substrates is only 0.01 to 1% of the $V_{max}/K_m$ measured for the polymer substrates.

The action of heparin lyases I-III on dermatan and chondroitin sulfates A–E was also studied. These substrates vary in position and degree of sulfation as well as the chirality of their uronic acid. The slight activity of these enzymes toward chondroitin sulfate C and dermatan sulfate suggested that either the heparin lyases are contaminated or that these substrates contained small amounts of heparin or heparan sulfate. To distinguish between these two possibilities, the reaction was followed for longer times. All of the activity was observed initially, after which the substrate became stable toward repeated challenges with fresh enzyme. This confirmed that the small activity observed was the result of contaminated substrate (approximately 1% heparin/heparan sulfate contamination in chondroitin sulfate C and dermatan sulfate) and not contaminated enzyme. None of the heparin lyases showed activity on hyaluronic acid. The failure of the heparin lyases to act on these other glycosaminoglycans clearly demonstrates both their specificity for heparin/heparan sulfate and the lack of contaminating lyase activity. No glycuronidase activity (Warnick, C. T., and Linker, A. (1972) Biochemistry 11, 568–572) was observed and less than 0.5% sulfatase activity (McLean, M. W., Bruce, J.s., Long, W. F., and Williamson, F. B. (1954) Eur. J. Biochem. 145, 607–615) was detected in the purified lyases.

II. Preparation of Monoclonal Antibodies to Heparinase I, Heparinase II, and Heparinase III.

Heparin lyase I was injected into mice and their B lymphocytes used to form monoclonal antibody-producing hybridomas. The specificity of the monoclonal antibodies (MAbs) for each of the three heparin lyases was examined.

MATERIALS AND METHODS

Preparation of heparin lyases for antibody production

Heparin lyases I, II and III were isolated from *Flavobacterium heparinum* and purified to homogeneity as described above. Heparin lyase concentrations were determined using a Bio-Rad Protein Assay Kit (Richmond, Calif., U.S.A.).

Preparation of monoclonal antibodies

Six monoclonal antibodies (mAbs) were prepared. Briefly, purified heparin lyase I was injected into mice three times over a period of 70 days. The mouse spleens were harvested and lymphocytes were isolated from the splenocyte mixture. The lymphocytes were fused with mouse myeloma cells to produce hybridomas. The hybridomas were cultured and screened for production of antibodies to heparin lyase I. Six hybridomas found to produce mAbs to heparin lyase I were designated M-1A, M2-B7, M2-A9, M-32, M-33, and M-34. Protein concentrations of the mAb solutions were determined using BCA Protein Assay Reagents from Pierce (Rockford, Ill., U.S.A.).

The concentrations of each monoclonal antibody is shown in Table IV.

TABLE IV

| MAb | MAb concentrations (mg/mL)[a] |
|---|---|
| M-32 | 49 |
| M-33 | 45 |
| M-34 | 41 |
| M-1A | 42 |
| M2-A9 | 44 |
| M2-B7 | 48 |

MAb solution protein concentration determined by BCA protein assay (Pierce).

Buffers for immunoassay procedures

Nitrocellulose membranes, Goat anti-Mouse IgG (H+L) Horseradish Peroxidase (HRP) Conjugate, Tris {hydroxymethyl} aminomethane (Tris), gelatin, Tween-20 and HRP Color Development Reagent (4-chloro-1-naphthol) were purchased from Bio-Rad (Richmond, Calif., U.S.A.). Tris buffered saline (TBS) was 20 mM Tris containing 500 mM sodium chloride, pH 7.5. Blocking solution was 3.0% gelatin in TBS. Tween-20 wash solution diluted in TBS (TTBS) was 0.05% Tween-20 in TBS. Antibody buffer was 1% gelatin in TBS. HRP color development solution was made by mixing 60 mg HRP Color Development Reagent in 100 mL methanol at 0° C. with 0.015° % $H_2O_2$ in TBS just prior to use.

Immunoassay analysis of heparin lyases using monoclonal antibodies

Dot-blotting immunoassay techniques were conducted as recommended in the Bio-Rad Immun-Blot Assay protocol (Bio-Rad, Richmond, Calif., U.S.A.). Briefly, nitrocellulose membranes were cut to 2×3 cm pieces and 1×1 cm squares were drawn on the membranes using a soft pencil. The membranes were soaked in TBS for 15 minutes and air dried on filter paper for 15 minutes. Various concentrations of the heparin lyase (1 μL in TBS) were placed in the center of each square and the membrane was air dried for 15 minutes, then the membrane was immersed in blocking solution for 1 hour to coat the remaining hydrophobic sites. This was washed four times in TTBS (two quick rinses, then two 5 minute agitations), then soaked overnight in a solution of mAb 0.2% (V/V) in antibody buffer, then the membranes were washed 4 times with TTBS and added to a solution of Goat anti-Mouse-HRP (0.1% in antibody buffer) for 4 hours with gentle agitation. The membranes were washed 4 times with TTBS, then twice with TBS. HRP color development solution was added to the membranes and when the purple bands were clearly visible, the development was stopped by placing the membranes in distilled water. The membranes were then dried on filter paper for 15 minutes and covered with aluminum foil to protect from light.

Electrophoresis

Materials

Electrophoresis was performed using a Mini-Protean II electrophoresis cell from Bio-Rad (Richmond, Calif., U.S.A.). Acrylamide and N,N'-methylene bisacrylamide were from International Biotechnologies Inc. (New Haven, Conn., U.S.A.) or used as a prepared 40% acrylamide solution that is 37.5 acrylamide:1 N,N'-methylene bisacrylamide (Fischer Scientific, Fairlawn, N.J., U.S.A.). Tris {hydroxymethyl} aminomethane (Tris) was from Bio-Rad (Richmond, Calif., U.S.A.). N,N,N',N'-Tetramethylethylenediamine (TEMED) was from Boehringer Mannheim Biochemicals (Indianapolis, Ind., U.S.A.). Ammonium persulfate (APS) and glacial acetic acid were from Mallinckrodt Inc. (Pads, Ky., U.S.A.). Urea and glycerol were from Fisher Scientific (Fair Lawn, N.J., U.S.A.). Sodium dodecyl sulfate (SDS) was from BDH Chemicals, Ltd. (Poole, England). Naphthol red was from Sigma Chemical Co. (St. Louis, Mo., U.S.A.). 2-β-mercaptoethanol was from EM Science (Gibbstown, N.J., U.S.A.). Bromophenol blue was from MCB Manufacturing Chemists, Inc. (Cincinnati, Ohio, U.S.A.). Molecular Weight Standards and Rapid Coomassie Stain were from Diversified Biotech (Newton Centre, Mass., U.S.A.)

SDS-polyacrylamide gel electrophoresis (PAGE)

Heparin lyases I, II, III and *Flavobacterium heparinum* cell homogenate were analyzed using SDS-PAGE as described above. Separating gels (12% acrylamide, 10% SDS) were prepared by mixing 4.35 mL distilled water, 2.5 mL of 1.5M Tris, pH 8.8 and 3.0 mL of a commercially prepared solution of 37.5 acrylamide:1 N,N'-methylene bisacrylamide (Fischer Scientific, Fairlawn, N.J., U.S.A.) as described above. This solution was degassed under vacuum for at least 15 minutes. Next, 50 μL of APS (10%) and 5 μL of TEMED were added to the monomer solution to initiate polymerization. The gel solution was quickly poured between two glass plates separated by 0.75 mm spacers, overlaid with distilled water saturated gamma-butanol and allowed to polymerize at 25° C. for 60 minutes.

Stacking gel was prepared by mixing 6.4 mL distilled water, 2.5 mL 0.5 M Tris, pH 6.8, 1.0 mL acrylamide/Bis solution (Fischer Scientific), 50 μL APS (10%) and 10 μL TEMED. The gamma-butanol was removed from the separating gel, the gel was rinsed with distilled water and the stacking gel solution was carefully added to the top of the separating gel. A well-forming electrophoresis comb was inserted in the stacking gel prior to polymerization. The stacking gel was allowed to polymerize for 60 minutes and the well-forming comb was removed just prior to loading of the samples.

Sample buffer was prepared by mixing 4.0 mL distilled water, 1.0 mL 0.5M Tris, pH 6.8, 0.8 mL glycerol, 1.6 mL SDS (10%), 0.4 mL 2-β-mercaptoethanol and 0.2 mL bromophenol blue (0.05% W/V). Samples and molecular weight standard markers for electrophoresis were diluted 1:4 in sample buffer and heated for 4 minutes at 100° C. just prior to loading into the wells formed earlier in the stacking gel. Running buffer (0.125M Tris, 1.0M glycine, 0.5% SDS, pH 8.3) was carefully overlaid on the stacking gel and the electrophoresis was conducted at a constant voltage of 200 V until the bromophenol blue marker moved to within 0.3 cm of the bottom of the gel (typically about 45 minutes). Following electrophoresis, the gels were either electro-transferred to nitrocellulose membranes or were stained with Rapid Coomassie Stain for 45 minutes followed by destaining with a 7.5% methanol/5% acetic acid solution.

Urea/Acetic Acid-PAGE

In some experiments, an urea/acetic acid-PAGE system (Panyim, S., and Chalkley, R. (1969) High resolution acrylamide gel electrophoresis of histones. *Arch. Biochem. Biophys.* 130, 337–346) was used instead of SDS-PAGE to compare the effects of SDS on the capacity of the mAbs to detect the heparin lyases in Western blots. Stock solutions used in the preparation of the urea/acetic acid-PAGE gels were prepared as follows. A 60% acrylamide solution was prepared by dissolving 60 g acrylamide and 0.4 g N, N'-methylene bisacrylamide in 1 00 mL of distilled water. A 43.2% acetic acid/TEMED stock solution was prepared by mixing 43.2 mL acetic acid, 4.0 mL TEMED and 52.8 mL distilled water. APS/urea was prepared by dissolving 5 mg APS in 25 mL of 1 0M urea.

The urea/acetic acid-PAGE gels were formed by mixing 4.0 mL of 60% acrylamide solution, 3.0 mL 43.2% acetic acid/TEMED and 2.0 mL distilled water. This solution and the APS/urea solution were degassed for 15 minutes. 15 mL of the APS/urea was added to the acrylamide monomer solution, mixed and carefully poured between two glass plates separated by two 0.75 mm spacers. A well-forming electrophoresis comb was inserted into the top portion of the gel and the gel was allowed to polymerize for 60 minutes.

The heparin lyases were diluted 1:4 in urea/acetic acid sample buffer. This sample buffer was prepared by mixing 520 μL acetic acid, 1.0 mL glycerol, 1.0 mg naphthol red, and 6.0 g urea in distilled water that was brought to a final volume of 10 mL. The well-forming comb was removed and samples were loaded into wells and overlaid with running buffer (0.9M acetic acid). Electrophoresis was conducted at a constant current of 20 mA for 3 hours (prefocusing of the gel) and then at 10 mA until the naphthol red moved to about 0.3 cm from the bottom of the gel (about 3 hours).

Electro-transfer of heparin lyases from acrylamide gels to nitrocellulose membranes Semi-dry transblotting was conducted using a SemiPhor Transfer Unit (TE-70) from Hoefer Scientific Instruments (San Francisco, Calif., U.S.A.). Electro-transfer of the heparin lyases from the SDS-PAGE or Urea/acetic acid-PAGE to nitrocellulose membranes was accomplished using Semidry transblotting techniques as described by Al-Hakim, A., and Linhardt, R. J. (1990) Isolation and recovery of acidic oligosaccharides from polyacrylamide gels by semi-dry electrotransfer. *Electrophoresis* 11, 23–28, except that 50 mM sodium phosphate, pH 6.8 was used as the transfer buffer. Transfer was accomplished in 40 minutes at 8 V.

Western blot detection of the heparin lyases using the monoclonal antibodies

Heparinases on the nitrocellulose membranes were detected using Western blotting techniques exactly as described above for dot-blotting immunoassay procedures.

Effects of SDS on detection of monoclonal antibodies

The effects of SDS and 2-β-mercaptoethanol on the immunodetection of the heparin lyases by mAbs M-32 and M-33 were examined. Dot-blotting immunoassays of heparin lyases I and II were performed as described earlier except that the heparin lyases were dissolved in solutions containing SDS and/or 2-β-mercaptoethanol in the same proportions used in SDS-PAGE analysis prior to blotting on the nitrocellulose membrane.

RESULTS

The reactivity of each of the six mAbs toward the three heparin lyases was examined. Varying amounts of each of the three heparin lyases were spotted on nitrocellulose membranes and detected using the anti-heparin lyase mAbs followed by addition of Goat anti-Mouse IGG-HRP and color development of the immune conjugates. Table V summarizes the lowest levels of each heparin lyases that were detected by immunoassay procedures. As seen in Table V, the mAbs have a broad range of sensitivities toward immunodetection of the three heparin lyases. For instance, M2-A9 and M2-B7 can detect as little as 10 pg of heparin lyase II, whereas M-32, M-33 and M-34 require the presence of 1 µg of heparin lyase III in order to detect that lyase.

TABLE V

| MAb | MAb detection of heparin lyases on nitrocellulose membranes[a] | | |
|---|---|---|---|
|  | Heparin lyase I | Heparin lyase II | Heparin lyase III |
| M-32 | 10 ng | 100 ng | 1 µg |
| M-33 | 10 ng | 10 ng | 1 µg |
| M-34 | 10 ng | 10 ng | 1 µg |
| M-1A | 100 pg | 100 pg | 10 ng |
| M2-A9 | 100 pg | 10 pg | 10 ng |
| M2-B7 | 100 pg | 10 pg | 10 ng |

[a]The minimum amount of each heparin lyase detectable by each of the six mAb using dot-blotting immunodetection.

These data demonstrate that mAbs can be used to distinguish between heparin lyases I and II when the two are present together, as in a *Flavobacterium heparinum* cell homogenate. Specifically, M-32 can detect levels of heparin lyase I that are ten times lower than heparin lyase II. Conversely, M2-A9 and M2-B7 can detect levels of heparin lyase II that are ten times lower than heparin lyase I. M-33, M-34 and M-1A cannot be used to distinguish between heparin lyases I and II. Furthermore, all six of the mAbs are able to detect much lower levels of heparin lyases I and II than of heparin lyase III, thus permitting distinction between heparin lyase III and heparin lyases I or II. Distinction between heparin lyases I and II is important because both enzymes can act on heparin and heparan sulfate and therefore are not easily distinguished based on their substrate specificity.

Western blot analysis of the heparin lyases

Figures 5A, 5B:
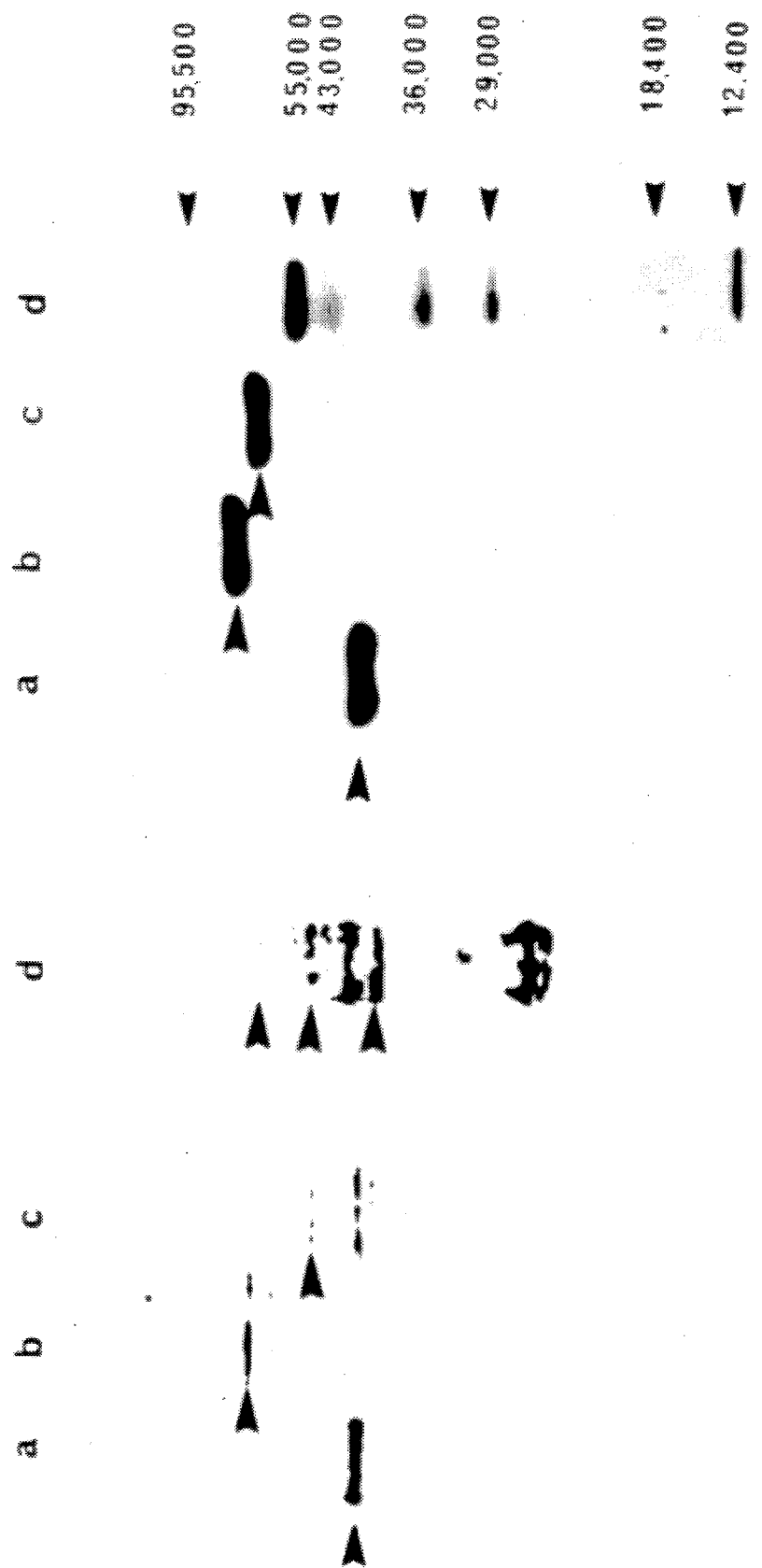
FIG. 5. Panel A: Western Blot of SDS-PAGE gel using M2-A9. (a) heparin lyase I; (b) heparin lyase II; (c) heparin lyase III; (d) *Flavobacterium heparinum* cell homogenate. Arrows indicate bands of interest. This analysis demonstrates the ability of this Mb to detect the presence of heparin lyases that are either purified or present in homogenized cellular material.

The three heparin lyases and *Flavobacterium heparinum* cell homogenate samples were analyzed on SDS-PAGE followed by Western blotting immunodetection, shown in FIG. 5a. FIG. 5b contains a typical SDS-PAGE gel of the three heparin lyases stained with Coomassie Blue along with molecular weight markers. The ability of mAbs to detect heparin lyases was examined by running the three heparin lyases and *Flavobacterium heparinum* cell homogenate through six SDS-PAGE gels followed by Western blotting immunodetection of the gel contents. Heparin lyase I (18 ng), heparin lyase II (570 ng), heparin lyase III (1.63 µg) and cell homogenate (87 ng) were loaded on each gel. The developing time used for detection on the nitrocellulose membrane containing M-34, M1-A, M2-A9 and M2-B7 were 20, 10, 15 and 40 minutes, respectively. Four of the mAbs (M-34, M-1A, M2-A9 and M2-B7) were able to detect purified heparin lyases I, II and III as well as heparin lyases present in the *Flavobacterium heparinum* cell homogenate. Two mAbs (M-32 and M-33) were not able to detect either the purified heparin lyases or cellular proteins in the Western blots.

The reagent in the SDS-PAGE system that was responsible for destroying the ability of M-32 and M-33 to immunodetect the heparin lyases was determined. Dot-blotting immunoassays of the heparin lyases using M-32 and M-33 were used to evaluate each component in the SDS-PAGE system. Heparin lyases I and II, in the presence or absence of SDS and/or 2-β-mercaptoethanol, were blotted on nitrocellulose membranes and examined using dot-blotting immunoassay techniques. The mAbs were unable to detect the lyases when SDS was present, demonstrating that SDS was responsible for the reduction of sensitivity of these two MAbs during the Western blotting procedures. This experiment suggests that M-32 and M-33 must be recognizing an epitope on the lyases that requires secondary conformation such as a folded structure present in all three heparin lyases that is destroyed by SDS denaturation.

To further demonstrate that the SDS was responsible for the diminished reactivity of M-32 and M-33 toward the heparin lyases, the three heparin lyases and *Flavobacterium heparinum* cell homogenate were analyzed using the urea/acetic acid-PAGE followed by Western blotting immunodetection with M-32 and M-33 to detect the lyases in this system. The sensitivity of detection was markedly reduced. Heparin lyase I (2.7 µg), heparin lyase II (3.4 µg), heparin lyase III (4.7 µg) and cell homogenate (7.7 µg) were detectable. Thus, SDS is the agent primarily responsible for the reduced reactivity of MAbs M-32 and M-33 toward the heparin lyases. All six MAbs are able to detect all three heparin lyases, in either the purified or the native form, when analyzed using PAGE followed by Western blotting immunodetection.

It was expected that at least one of the six MAbs would specifically detect a single heparin lyase, enabling the detection of that lyase in a complex mixture of heparin lyases such as a cell homogenate. The dot-blotting and Western analyses revealed that all of the mAbs are able to detect all three lyases. This observation suggests that these three heparin lyases are remarkably similar in structure since they share six common epitopes. Peptide mapping of these three enzyme demonstrates a number of common peptide fragments and suggests that these may be located at the highly immunogenic regions within the three heparin lyases. The sensitivities of individual mAbs toward each of the lyases in the dot-blotting analyses varied greatly, thus offering the potential to use the dot-blotting analysis to distinguish between the three lyases.

Use of PAGE (SDS or urea/acetic acid) required much more protein than dot-blotting procedures and the sensitivities of the mAbs toward each of the lyases were different than those seen in the dot-blotting analyses, probably due to alterations of secondary structure during the PAGE and transfer steps. Thus, detection of heparin lyases using mAbs is most efficiently conducted by use of dot-blotting techniques as described here. Furthermore, all six MAbs were able to detect all three lyases that were present in *Flavobacterium heparinum* cell homogenate, thus offering the potential that these mAbs could be used to rapidly demonstrate the presence of heparin lyases in cell homogenate. To be beneficial in lyase purification, these MAbs must first be immobilized and their binding activity to the heparin lyases assessed. Methods and materials for immobilization of antibodies are commercially available and known to those skilled in the art.

In summary, the results described here demonstrate that mAbs can be used to detect heparin lyases I, II and III in either their purified state or when present together in a solution of homogenized Flavobacterial cells. These mAbs can also be used in dot-blotting analyses of the lyases to distinguish between the three lyases based on their different sensitivity for each of the three lyases.

Modifications and variations of the purified heparinases, method of purification and monoclonal antibodies thereto will be obvious to those skilled in the art from the foregoing detailed description. Such modifications and variations are intended to come within the scope of the appended claims.

We claim:

1. A method for cleaving hexosamine-glucuronic acid linkages in linear polysacharides of D-glucosamine linked to hexuronic acid comprising reacting heparin or heparan sulfate with a purified heparinase selected from the group consisting of heparinase II present in *Flavobacterium heparinum* free of lyase activity other than heparinase II activity, having a molecular weight of 84,100, cleaving heparin and heparan sulfate and having a pH optimum of 8.9–9.1 and heparinase III which is expressed in *Flavobacterium heparinum* free of lyase activity other than heparinase III activity, having a molecular weight of 70,800, cleaving heparan sulfate, and having a pH optimum of 9.9–10.1.

2. The method of claim 1 wherein the heparin is in extracellular matrix of cells or tissues.

* * * * *